US00PP14448P29

(12) United States Plant Patent
Smith

(10) Patent No.: US PP14,448 P2
(45) Date of Patent: Jan. 6, 2004

(54) APPLE TREE: 'SMITH GALA'

(50) Latin Name: *Malus domestica*
Varietal Denomination: Smith Gala

(76) Inventor: Joe Smith, 13477 Locust La., Nampa, ID (US) 83651

( * ) Notice: Subject to any disclaimer, the term of this patent is extended or adjusted under 35 U.S.C. 154(b) by 126 days.

(21) Appl. No.: 09/939,283

(22) Filed: Aug. 23, 2001

(51) Int. Cl.[7] ..... A01H 5/00

(52) U.S. Cl. ..... Plt./162

(58) Field of Search ..... Plt./162

(56) References Cited

U.S. PATENT DOCUMENTS

PP4,121 P 10/1977 Ten Hove
PP11,348 P * 4/2000 McSpadden, Jr. ..... Plt./162
PP13,753 P2 * 4/2003 Banning ..... Plt./162

* cited by examiner

*Primary Examiner*—Bruce R. Campell
*Assistant Examiner*—W C Haas
(74) *Attorney, Agent, or Firm*—Christensen O'Connor Johnson Kindness PLLC

(57) ABSTRACT

A new and distinct variety of apple tree which originated as a branch mutation of 'Tenroy cultivar' Royal Gala® apple tree (U.S. Plant Pat. No. 4,121), characterized by larger fruit with thicker stem and later bloom time as compared to the parent.

5 Drawing Sheets

Botanical classification: *Malus domestica.*

FIELD OF THE INVENTION

The invention relates to a new and distinct variety of apple tree, *Malus domestica,* which originated as a branch mutation of the 'Tenroy cultivar' Royal Gala® apple tree (U.S. Plant Pat. No. 4,121).

BACKGROUND OF THE INVENTION—DISCOVERY AND ASEXUAL REPRODUCTION OF THE TREE

The new variety, denominated 'Smith Gala,' was discovered by Joe Smith at his orchard located at 13477 Locust Lane, Nampa, Id. The tree having the mutated branch was found in a cultivated block of Royal Gala® ('Tenroy cultivar') apple trees with appropriate pollinators.

Mr. Smith was attracted to the tree by the single limb that had fruit noticeably larger than, but otherwise similar to, the remainder of the tree and neighboring trees. The new variety is up to 15% larger, 40% heavier, and with a more oblate shape (lower L/D ratios) than fruit of the parent Royal Gala®. The new variety has been observed to bloom approximately three days later than its parent Royal Gala® tree, and has a thicker stem than other known 'Gala' cultivars. Fruit from the new variety is identical to that of its parent in taste and texture. Asexual reproduction of the 'Smith Gala' tree was successfully accomplished in August 1995 when Mr. Smith budded one tree on Malling No. 7 rootstock at his home orchard. In August 1996, 3 trees were budded on Malling No. 26 rootstock in the test orchard of Van Well Nursery, Inc., located at 2821 Grant Road, Wenatchee, Wash., and 46 trees were budded on Malling 26 rootstock in the nursery of Van Well Nursery, Inc., at the same address. The nursery trees were planted in the spring of 1998. The test orchard trees (second generation) bore fruit in 1999 and 2000, and of the 46 nursery trees planted in the spring of 1998 (also second generation), approximately 30 bore fruit in 2000. Fruit of the second generation trees is identical to that of its parent.

BRIEF SUMMARY OF THE INVENTION

The new variety has been compared to the parent tree, Royal Gala®, 'Tenroy cultivar'. These comparisons are from the second generation trees growing at the orchard of Van Well Nursery, Inc., in Wenatchee, Wash. Physical and internal characteristics of the new variety and the parent are shown in Table 1 for apples picked in September 1999, and in Table 2 for apples picked in September 2000. Average diameter of apples of the new variety is approximately 7% to approximately 15% greater than that of Royal Gala® fruit; the length is slightly less (approximately 1.4% to approximately 7.9% less); and the fruit weight as measured in 2000 was approximately 39% greater. The difference in diameter is equivalent to 3 box sizes (from 100's to 72's) larger for the new variety as compared to Royal Gala® fruit. Samples of vegetative shoots were compared (see FIG. 4) and it appeared that the leaves of the new variety were slightly larger on average than those of Royal Gala®. At harvest time, the new variety exhibited a thicker stem (approximately 5 mm in diameter as compared to approximately 3 mm for other 'Gala' cultivars—see FIG. 6). In April 2000, it was observed that full bloom for the new variety was approximately 3 days later than for Royal Gala® trees.

TABLE 1

(1999)

| | 'Smith cv.' | 'Tenroy cv.' |
|---|---|---|
| Length (cm) | 6.86 | 6.96 |
| Diameter (cm) | 8.60 | 7.45 |
| L/D Ratio | 0.798 | 0.934 |
| Firmness (#) | 17.2 | 18.4 |
| Soluble Solids | 15.2% | 13.2% |
| Starch (1–6 scale) | 4.7 | 3.5 |

TABLE 2

| | (2000) | |
|---|---|---|
| | 'Smith cv.' | 'Tenroy cv.' |
| Weight (gm) | 2.84 | 2.04 |
| Length (cm) | 7.00 | 7.55 |
| Diameter (cm) | 8.57 | 8.02 |
| L/D Ratio | 0.817 | 0.941 |
| Firmness (#) | 16.7 | 16.8 |
| Soluble Solids (%) | 12.9 | 13.0 |
| Starch (1–6 scale) | 3.0 | 2.5 |

BRIEF DESCRIPTION OF THE DRAWINGS

The accompanying photographs show the following characteristics of this new variety.

DETAILED BOTANICAL DESCRIPTION OF THE TREE

Figure 1:
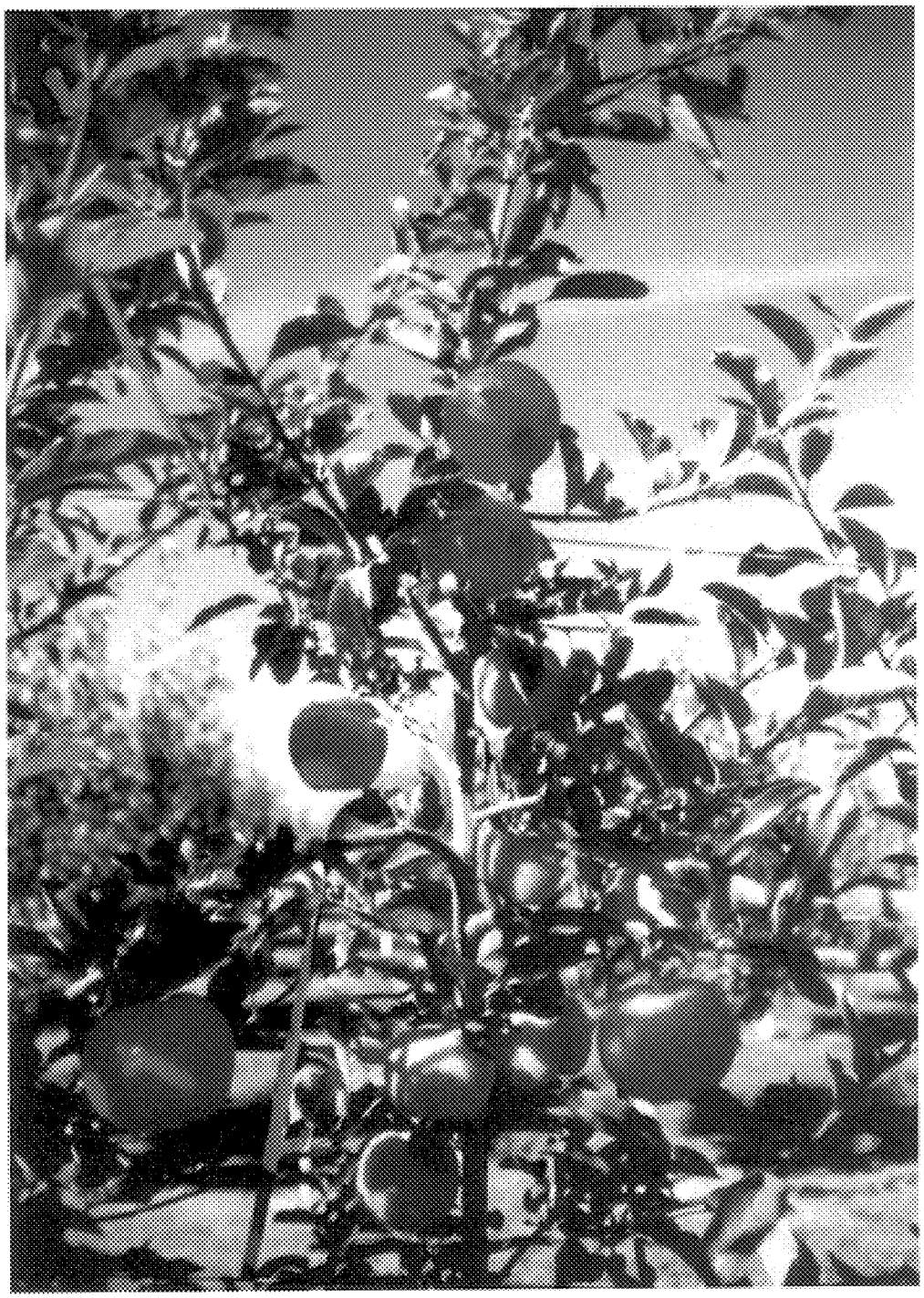
FIG. 1 shows typical fruit of the new variety on the tree, as observed in September 1999 at East Wenatchee, Wash.
Figure 2:
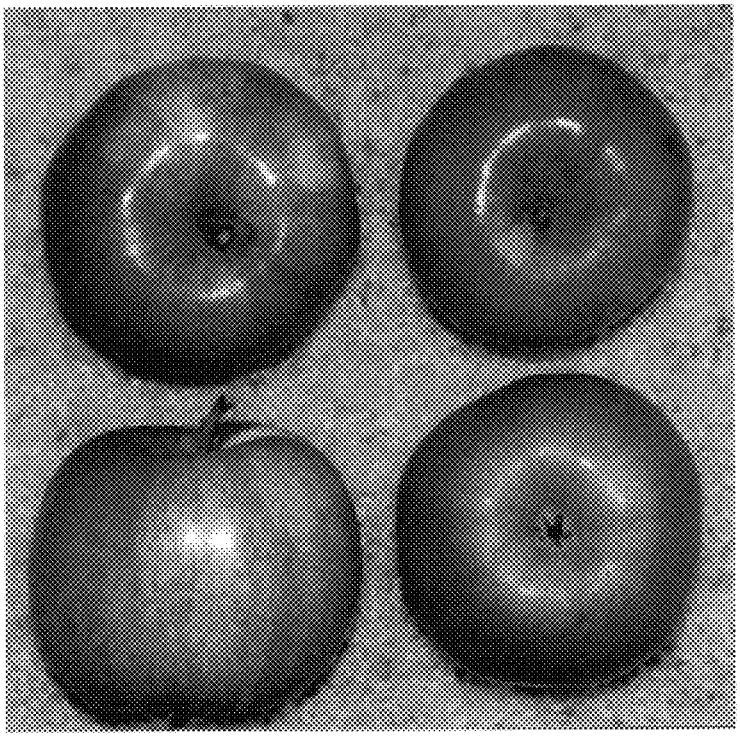
FIG. 2 shows individual fruits of the new variety taken from the tree of FIG. 1, showing the general shape and appearance of the cavity and calyx, the fruit having been picked approximately 3 weeks after the photograph of FIG. 1.
Figure 3:
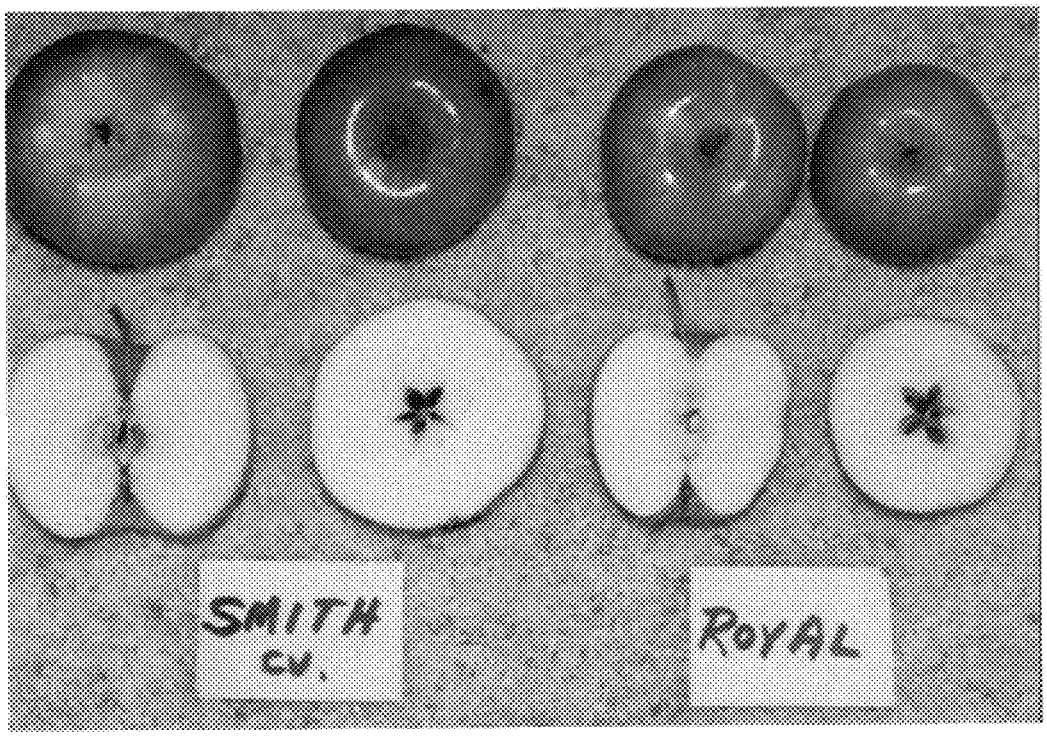
FIG. 3 compares apples of the new variety (left) with apples of the parent (right), the fruit appearing substantially identical except for the larger size and more oblate shape of the new variety (photo taken on the same date as FIG. 2).
Figure 4:
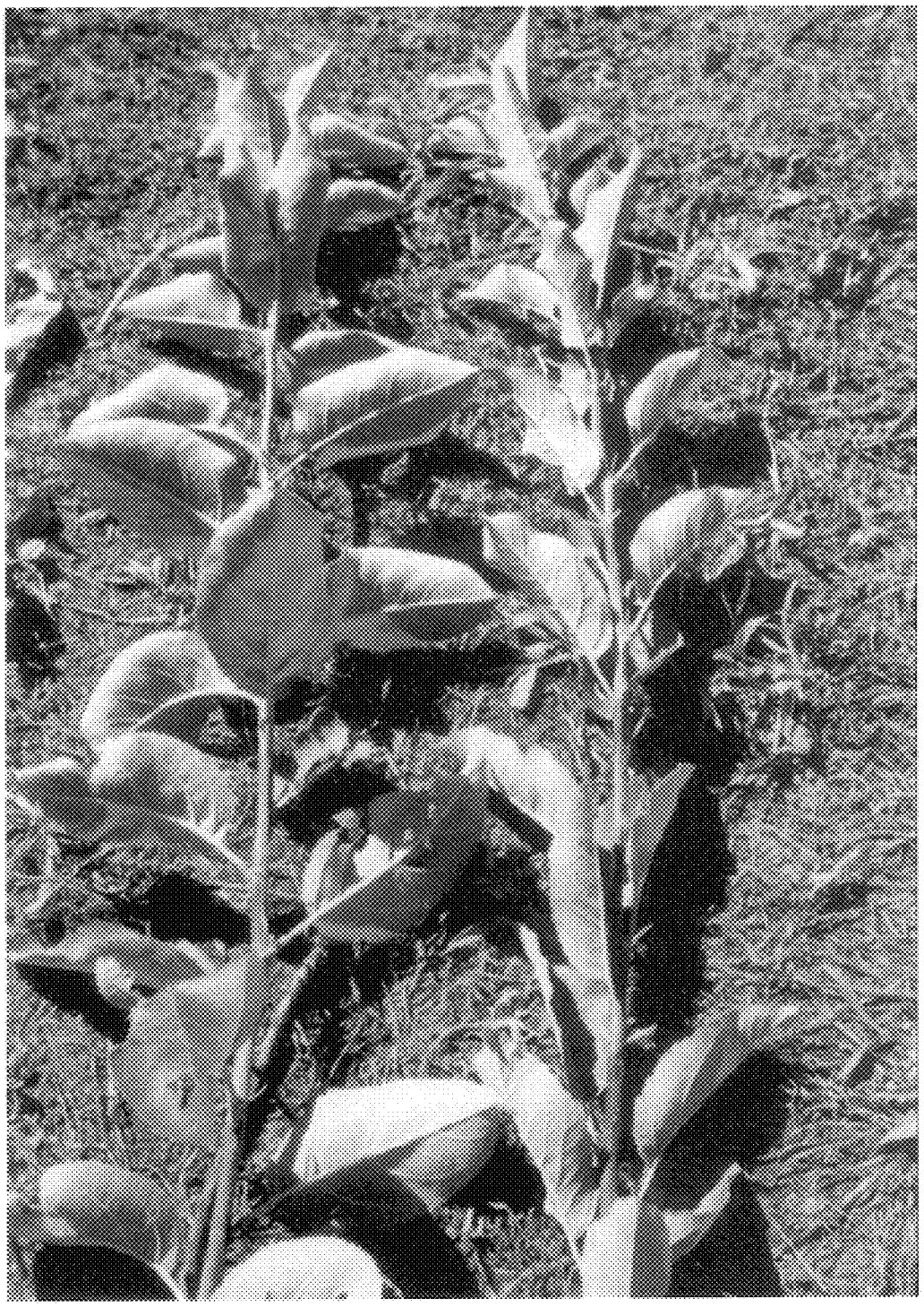
FIG. 4 compares a new vegetative shoot of the new variety (left) with its parent (right), the leaves of the new variety appearing slightly larger, photograph taken a few days before the photograph of FIG. 1.
Figure 5:
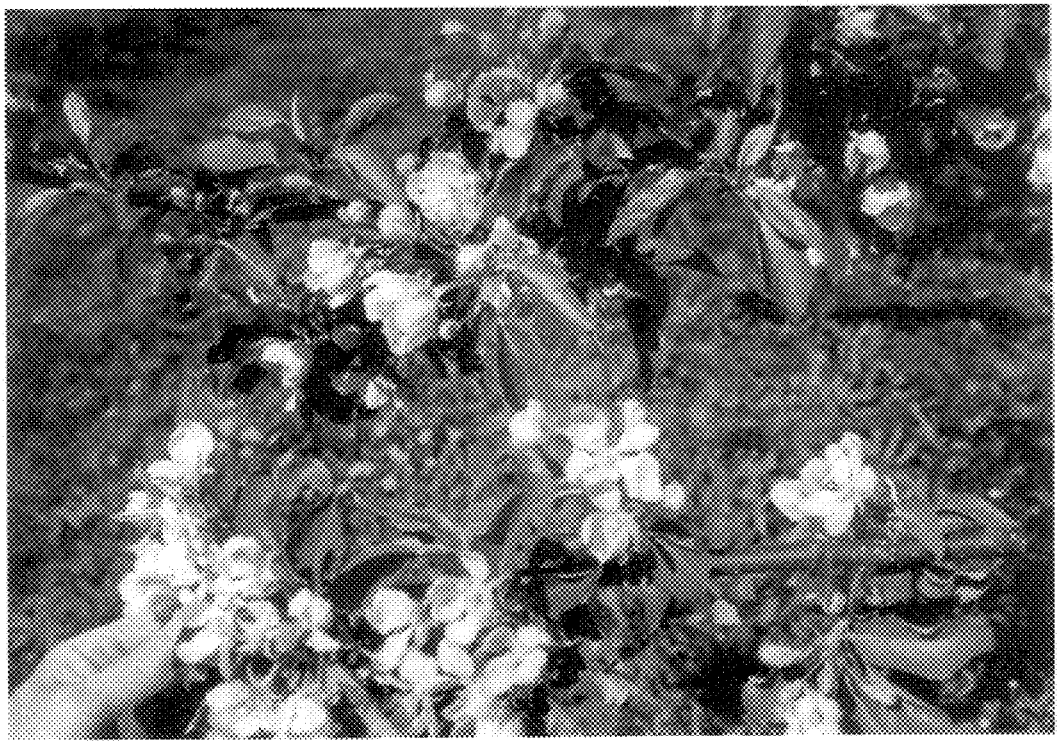
FIG. 5 compares a branch of the parent (bottom) in full bloom (April 2000) to a branch of the new variety (top) which reached an equivalent full bloom approximately 3 days later.
Figure 6:
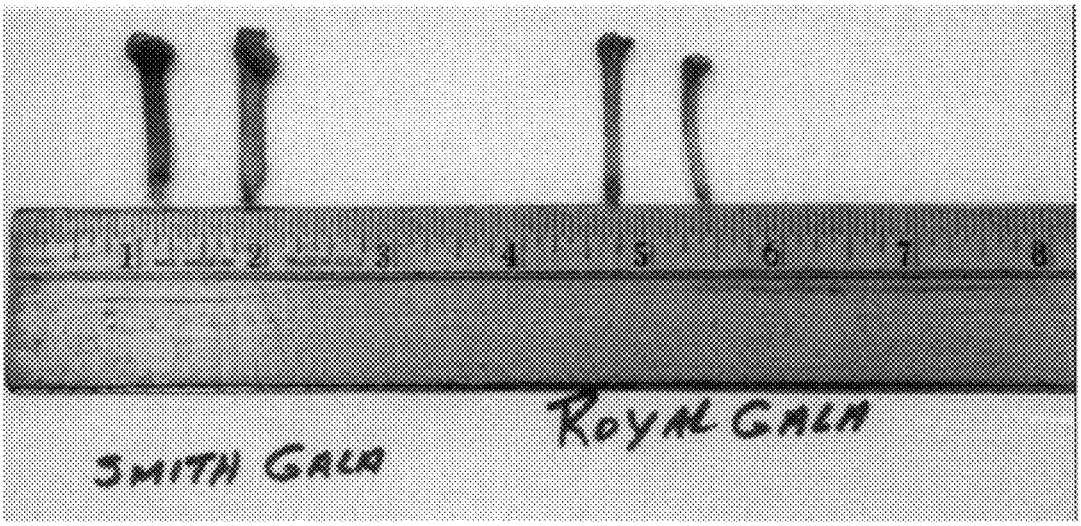
FIG. 6 compares stem size for the new variety (left) with stem size of the parent (right), showing the larger diameter stems of the new variety.

Unless indicated otherwise, information is for a five-year old tree on its sixth leaf, grown in East Wenatchee, Wash., on M-26 rootstock. The tree was planted in 1996.

Parentage: Branch mutation of Royal Gala® 'Tenroy cultivar' (U.S. Plant Pat. No. 4,121) discovered at Nampa, Id., in cultivated Royal Gala® block by Joe Smith.

Maturity date: September 5 to 10 at Wenatchee, Wash.

Tree: Semi-dwarf size, between 9 and 10 feet tall and approximately 4 feet wide; High vigor, 70 to 100 cm annual new shoot growth in Wenatchee in 1999; General upright to globe shape; Round-topped; Hardy; Productive, production for trees in their 7th leaf averaged 3 boxes per tree; Regular bearer.

*Susceptibility to insects.*—Medium (similar to other 'Gala' varieties).

*Susceptibility to diseases.*—Medium (similar to other 'Gala' varieties).

Trunk: Stocky; medium, 8 inches in circumference 1 foot above the ground; smooth when young, becoming rough as tree ages; gray to light brown (7.5 YR 6/2, Munsell Book of Color (hereinafter referred to as "Munsell")).

Branches: Medium thickness, lower scaffold branch at 4 feet above the ground and 7 inches from the central leader averaged 2.87 inches in circumference; upright to slightly spreading, becoming more spreading with age; gray (5 YR 4/2 Munsell) darkening with age (2.5 YR 3/2 Munsell); oval, sparse, tan lenticels (7.5 YR 8/2 Munsell) of medium size (about 1 mm) average length internodes (25 to 35 mm on 1-year shoots).

*Pubescence.*—Light gray (2.5 YR 7/2 Munsell).

Flowers: Similar in appearance to parent 'Tenroy cv'; first bloom in mid-season on Apr. 18, 2000, full bloom in midseason on Apr. 27, 2000; 9 to 10 days bloom duration; opening flower is light pink (2.5R 7/6 Munsell) with large, showy blooms (55 mm) almost white, retaining a slight pink color at full bloom.

*Petals.*—Five in number, touching to overlapping; single row stamen, average 25 to 30 per blossom, bright yellow (2.5Y 8.5/12 Munsell) anthers.

*Pistil.*—Stigma medium length and branched at top into five elements, stiles medium (12 mm) fused at base.

*Sepals.*—Five in number, 12 mm long×5 mm wide at base, pale green (10GY 7/2 Munsell), pubescent; light fragrance.

*Buds.*—Small, short, conical-plump, approximately 10 mm long by approximately 5 mm wide, light pink (2.5 R 7/6 Munsell).

Leaves: Similar to 'Tenroy cv.'; glossy on upper surface, finely pubescent on lower surface; medium size: average of 25 leaves sampled September 1999: 89 mm (65 to 100 mm) long, 50 mm (45 to 55 mm) wide; medium petiole, average 17 mm (15 to 20 mm), finely pubescent; finely serrate, acute to acuminate tip, acute base shape, 2 stipules averaging 10 mm in length, dark green (upper surface 5 GY 3/6 Munsell; lower surface 5 GY 6/4 Munsell).

Fruit: (average of 10 fruits in 1999): Mid-harvest maturity September 10; pressure average — 17.2 lbs.; soluble solids — 15.2%; starch rating — 4.7; 0.5% malic acid; large, 8.6 cm (box size 72).

*Stem cavity.*—Medium width (35 mm), deep (22 mm), acute to acuminate.

*Basin cavity.*—Broad (35 mm), medium depth (10 mm), obtuse.

*Stem.*—Medium to long (35 to 42 mm), thick (5 mm).

*Locules (carpels).*—Small to medium size (average 25 mm), slightly open, 5 in number,; smooth skin with slight bloom, shiny but without greasiness, occasional flaring russett in stem cavity, medium thin, tendency to stem-end cracking as fruit becomes overmature; cream-colored (5 Y 9/4 Munsell) lenticels up to 1 mm in size, round, similar to 'Tenroy cv.';

*General color effect.*—Bright pinkish red to red stripes over yellow ground color, similar to 'Tenroy cv.'.

*Ground color.*—5 Y 9/6 Munsell.

*Overcolor.*—Red stripe (60–80% 5 R 3/10 Munsell).

*Flesh.*—Cream-color (5 Y 9/4 Munsell), very juicy, sweet, 12 to 15% soluble solids, non-astringent, sprightly flavor, low acidity (approximately 0.5% malic acid), medium to strong aroma (good apple aroma), 16.6 to 17.4 lbs. firmness at harvest, crisp, non-melting texture.

*Core.*—Bundle area round, 40 mm average width, 35 mm average length, core lines weakly defined, calyx tube closed, cell walls fairly thick (slow to break down in mouth, adding to the crunchy sensation).

*Seed.*—Similar to 'Tenroy cv.', 2 per cell, obovate, dark brown (7.5 YR 9/2), 8 mm length×4 mm width, loosely adhering to the carpel wall; keeping quality similar to 'Tenroy cv.': quality maintained up to 3 months in common storage (0° C.) and up to 5 months in controlled atmosphere storage, fruit remains firm and crisp at room temperature for at least one week.

Usage: Primarily fresh eating or dessert, identical to 'Tenroy cv.'

I claim:

1. A new and distinct variety of apple tree substantially as herein shown and described.

* * * * *